US 6,642,478 B2

(12) United States Patent
Nishida et al.

(10) Patent No.: US 6,642,478 B2
(45) Date of Patent: Nov. 4, 2003

(54) METHOD FOR FORMING A VIA HOLE, FLEXIBLE WIRING BOARD USING THE METHOD, AND METHOD FOR PRODUCING THE FLEXIBLE WIRING BOARD

(75) Inventors: Kanji Nishida, Ibaraki (JP); Hitoshi Ishizaka, Ibaraki (JP); Atsushi Hino, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 10/251,820

(22) Filed: Sep. 23, 2002

(65) Prior Publication Data

US 2003/0057193 A1 Mar. 27, 2003

(30) Foreign Application Priority Data

Sep. 26, 2001 (JP) .......................................... 2001-294956

(51) Int. Cl.[7] .............................................. B23K 26/38
(52) U.S. Cl. .............................. 219/121.71; 219/121.76
(58) Field of Search .......................... 219/121.6, 121.65, 219/121.66, 121.67, 121.68, 121.69, 121.7, 121.71, 121.72, 121.76, 121.85

(56) References Cited

U.S. PATENT DOCUMENTS 5,820,648 A * 10/1998 Akaike et al.
6,414,263 B1 * 7/2002 Uchida et al.

* cited by examiner

Primary Examiner—Samuel M. Heinrich
(74) Attorney, Agent, or Firm—Sughrue Mion, PLLC

(57) ABSTRACT

An ultraviolet beam with high energy density is applied for forming an opening in an electric conductor layer 1 in a flexible wiring board whereas an ultraviolet beam with low energy density is applied for forming an opening in an electrically insulating layer 2 in the flexible wiring board. As a result, excessive heat energy applied for forming a via hole can be reduced, so that the problems can be reduced. In this manner, high quality of the via hole and delicate and accurate processability due to use of the ultraviolet laser beam can be combined to achieve formation of fine patterns densely in the flexible wiring board.

7 Claims, 4 Drawing Sheets

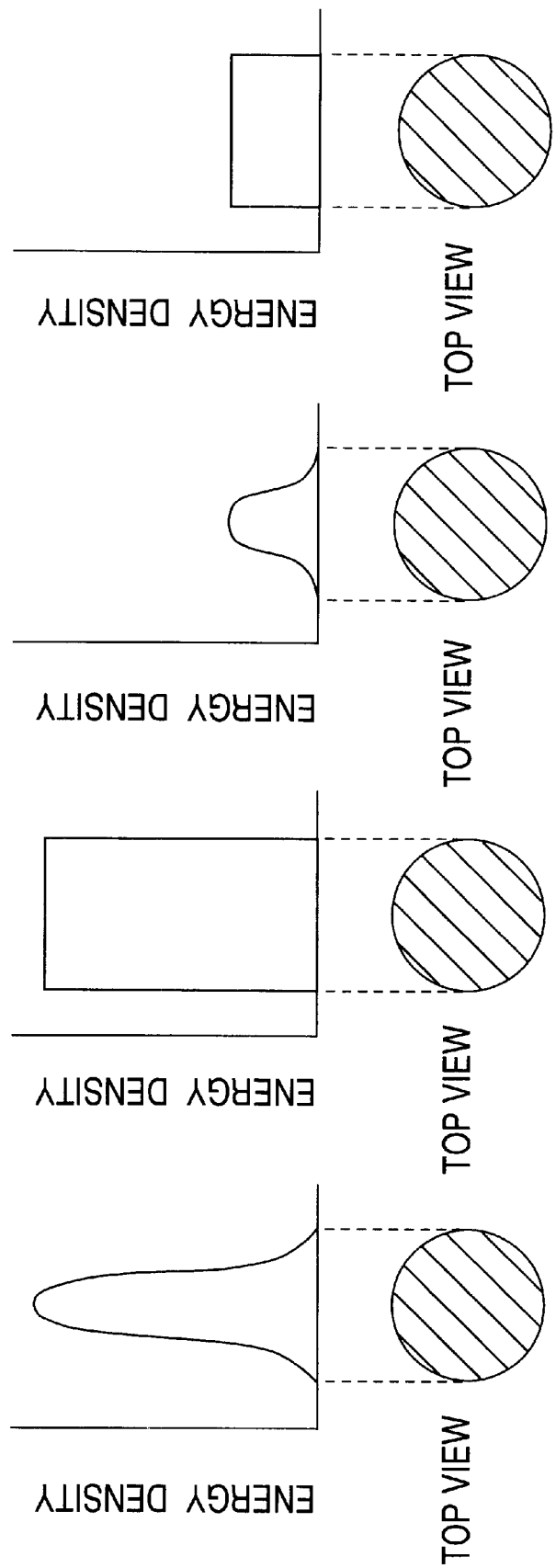

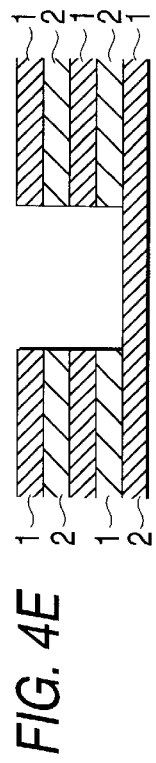
FIG. 4E
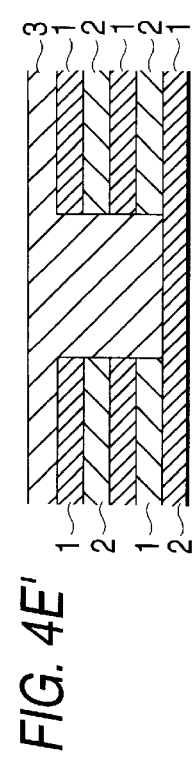
FIG. 4E'
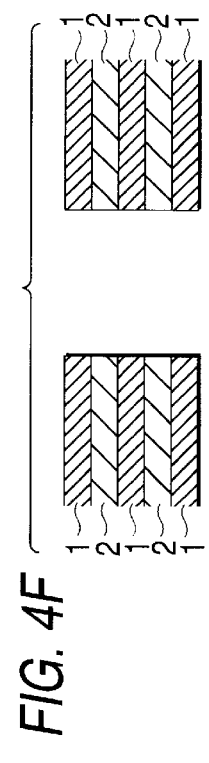
FIG. 4F
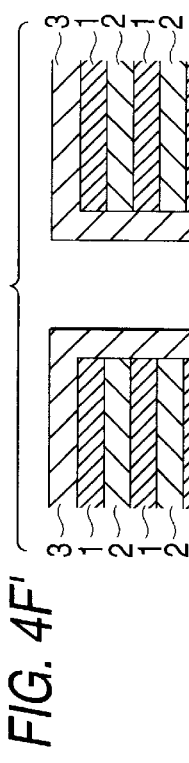
FIG. 4F'
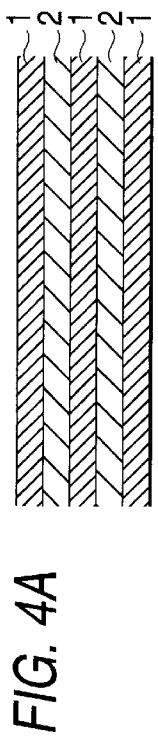
FIG. 4A
FIG. 4B
FIG. 4C
FIG. 4D

METHOD FOR FORMING A VIA HOLE, FLEXIBLE WIRING BOARD USING THE METHOD, AND METHOD FOR PRODUCING THE FLEXIBLE WIRING BOARD

The present application is based on Japanese Patent Application No. 2001-294956 filed on Sep. 26, 2001, the entire contents of which are incorporated herein by reference.

BACKGROUND OF THE INVENTION

1. Field of the Invention

The present invention relates to a flexible wiring board used in electronic apparatus such as a portable terminal apparatus, and a method for producing the flexible wiring board, particularly, a method for forming a via hole in the flexible wiring board.

2. Description of the Related Art

The mobile and wearable demand for portable terminal apparatus such as cellular phones has increased with the remarkable advance of technological innovation in recent years. Flexible wiring boards have been required to be finely patterned and densely provided with the advance of reduction in weight and thickness and increase in density of the electronic apparatus.

Reduction in size and pitch of electric connection portions is required for patterning a flexible wiring board finely. Formation of three-dimensional wiring in a flexible wiring board is also required for increasing density. That is, because the flexible wiring board is a laminate of layers constituted by wiring boards having desired circuit patterns, the flexible wiring board needs to have a structure in which the layers are electrically connected to one another through via holes subjected to a plating process. Therefore, reduction in pitch and size of the via holes used for such electric connection is required for achieving both fine patterning and increase in density simultaneously.

When both pitch and size of the via holes are reduced as described above, reliability of electric connection after the plating process is largely influenced by the quality of the processed via holes. However, if the via holes are formed by a drill, burrs are generated. If the via holes are formed by an infrared laser beam, the electric conductor layer does not absorb the infrared laser beam so that the electrically insulating layer is damaged by heat accumulated in the via holes. Hence, greater reduction in size of the via holes can be hardly achieved by use of a drill or an infrared laser beam because of the problems in projections on the electric conductor layer and damage of the electrically insulating layer.

Therefore, a method of forming a via hole by an ultraviolet laser beam has been used in recent years, so that the formation of fine-size via holes has been realized. It is however impossible to perfectly solve the problems in burrs or projections and deposition of smears even in the case where an ultraviolet laser beam is used. To achieve greater reduction in size of the via holes, a proposal for a forming method to reduce these problems is desired.

SUMMARY OF THE INVENTION

In consideration of such circumstances, an object of the invention is to propose a method for forming a via hole substantially free from these problems to thereby make it possible to achieve reduction in pitch and size of the via hole and to provide a flexible wiring board which meets the requirements of finer patterning and increase in density.

The present inventors have made researches into solution of the problems while paying attention to energy density of an ultraviolet laser beam applied on a via hole-forming portion. As a result, the invention having the following features has been already accomplished.

(1) A method of forming a via hole in a flexible wiring board having at least two electric conductor layers and at least one electrically insulating layer for insulating said two electric conductor layers from each other, said method comprising:

irradiating one of said electric conductor layers with a first ultraviolet laser beam; and irradiating said electrically insulating layer with a second ultraviolet laser beam;

wherein energy density of said first ultraviolet laser beam is higher than energy density of said second ultraviolet laser beam.

(2) A method of forming a via hole in a flexible wiring board according to (1), wherein energy density of said first ultraviolet laser beam is selected to be higher by a value ranged from 0.1 to 20 J/cm$^2$ than energy density of said second ultraviolet laser beam.

(3) A method of forming a via hole in a flexible wiring board according to (1) or (2), wherein energy density of said first ultraviolet laser beam is selected to be in a range of from 5 to 20 J/cm$^2$, whereas energy density of said second ultraviolet laser beam is selected to be in a range of from 0.05 to 5 J/cm$^2$.

(4) A method of forming a via hole in a flexible wiring board according to (1) through (3), said method comprising the steps of:

irradiating a via hole-forming portion of said one of said electric conductor layers with said first ultraviolet laser beam to thereby form an opening in said one electric conductor layer; and subsequently irradiating said electrically insulating layer with said second ultraviolet laser beam to thereby form an opening in said electrically insulating layer after forming the opening in said one electric conductor.

(5) A method of forming a via hole in a flexible wiring board by repeating the steps defined in (4).

(6) A method of forming a via hole in a flexible wiring board according to (1) through (3), said method comprising the steps of:

irradiating a via hole-forming portion of a first layer of said electric conductor layers with said first ultraviolet laser beam to thereby form an opening in said first electric conductor layer; and irradiating said electrically insulating layer with said second ultraviolet laser beam to thereby form an opening in said electrically insulating layer; and irradiating a second layer of said electric conductor layers which is located on opposite side to said first electric conductor layer with respect to said electrically insulating layer with said first ultraviolet laser beam to thereby form an opening in said second electric conductor layer, whereby said openings are formed as the via hole in said flexible wiring board.

(7) A method of producing a flexible wiring board, including a method defined in any one of (1) through (6).

(8) A flexible wiring board produced by a method defined in (7).

BRIEF DESCRIPTION OF THE DRAWINGS

FIGS. 1A to 1D are typical views showing examples of energy density and irradiation range of an ultraviolet laser beam used in the invention;

FIGS. 4A to 4F' are explanatory views showing a further example of the method for forming a via hole according to the invention.

DETAILED DESCRIPTION OF THE PREFERRED EMBODIMENTS

Figure 2A:
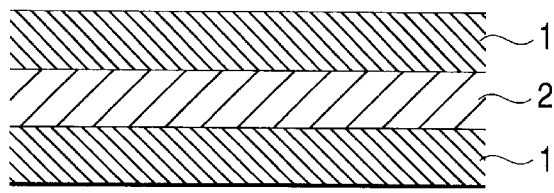
FIGS. 2A to 2D are explanatory views showing an example of the method for forming a via hole according to the invention.

The invention will be described below suitably with reference to the drawings but the invention is not at all limited to the mode shown in the drawings. Description will be made in such an order that an ultraviolet laser used for forming a via hole will be described as a feature of the invention before the configuration (such as material, shape, etc.) of a flexible wiring board according to the invention is described.

An ultraviolet laser beam with a wavelength in a range of from 200 to 400 nm, preferably in a range of from 240 to 360 nm is used for forming a via hole in the invention. Both an electric conductor layer and an electrically insulating layer in a flexible wiring board are irradiated with the ultraviolet laser beam having the following energy density to form openings in the two layers to thereby form a via hole in the flexible wiring board. As the ultraviolet laser beam, there can be used a known laser beam such as a third harmonic laser beam (wavelength: 355 nm) of an Nd:YAG laser, a laser beam (wavelength: 351 nm) of an excimer laser (XeF) or a laser beam (wavelength: 249 nm) of an excimer laser (XrF).

Energy of the applied ultraviolet laser beam will be described with reference to FIGS. 1A to 1D. FIGS. 1A to 1D are typical views showing examples of energy density and irradiation range of the ultraviolet laser beam used in the invention. Irradiation with the ultraviolet laser beam used for suitably processing an electric conductor layer in a flexible wiring board is selected to have an energy density (FIGS. 1A and 1B) higher than the energy density (FIGS. 1C and 1D) of the ultraviolet laser beam used for processing an electrically insulating layer. Preferably, the former energy density is selected to be higher by a value of 0.1 to 20 J/cm$^2$ than the latter energy density. Especially preferably, the former energy density is selected to be higher by a value of 3 to 8.5 J/cm$^2$ than the latter energy density. In a general laser beam generator, such energy density can be controlled easily by adjustment of voltage applied to the laser beam source and irradiation size of the laser beam. Specifically, the energy density of the laser beam used for processing an electric conductor layer is preferably in a range of from 5 to 20 J/cm$^2$, especially preferably in a range of from 6 to 10 J/cm$^2$ whereas the energy density of the laser beam used for processing an electrically insulating layer is preferably in a range of from 0.05 to 5 J/cm$^2$, especially preferably in a range of from 1.5 to 3 J/cm$^2$. In addition, it is preferable that a laser beam with uniform energy density is applied on a target surface to be processed. That is, a laser beam with energy density shown FIG. 1B rather than energy density shown in FIG. 1A is used for processing an electric conductor layer whereas a laser beam with energy density shown FIG. 1D rather than energy density shown in FIG. 1C is used for processing an electrically insulating layer. To obtain laser beams shown in FIGS. 1B and 1D, there may be used a known beam-shaping optical system such as a micro lens array or a masked projection system.

When the energy density of the ultraviolet laser beam applied on an electric conductor layer is selected to be high, protrusions can be prevented from being produced in the periphery of the processed hole and the processing time can be shortened. On the other hand, when the energy density of the ultraviolet laser beam applied on an electrically insulating layer is selected to be low, excessive ultraviolet laser beam irradiation can be suppressed so that generation of heat can be reduced. As a result, damages of the peripheral electric conductor layer and the peripheral electrically insulating layer can be suppressed. Moreover, an interlayer peeling phenomenon caused by heat can be suppressed. Hence, it is possible to form a processed hole which is so good in quality of processing that production of protrusions can be suppressed. The processed hole good in quality of processing can prevent nonconformity in a post-process such as uneven electro-deposition in a plating process. This is very useful for forming fine patterns densely in the flexible wiring plate.

The flexible wiring board according to the invention will be described below with reference to FIGS. 2A to 2D, FIGS. 3A to 3E and FIGS. 4A to 4F'. FIGS. 2A to 2D, FIGS. 3A to 3E and FIGS. 4A to 4F' are explanatory views showing examples of the method for forming a via hole according to the invention. The flexible wiring board according to the invention has at least one structure in which two electric conductor layers 1 as predetermined circuit patterns are provided on opposite surfaces of an electrically insulating layer 2 and electrically connected to each other by a via hole.

The simplest mode of the flexible wiring board is a so-called double face circuit board in which circuit patterns of electric conductor layers 1 are formed on opposite surfaces of an electrically insulating layer 2 as shown in FIGS. 2A to 2D. The concept "flexible wiring board" used herein includes a board, for example, of a five-layer structure in which electric conductor layers 1 and electrically insulating layers 2 are laminated alternately as shown in FIGS. 4A to 4F'. The scope of the invention further includes a flexible wiring board (not shown) having two or more electrically insulating layers 2, and a flexible wiring board (not shown) having electrically insulating layers 2 as outermost layers instead of electric conductor layers 1.

Figure 2B:
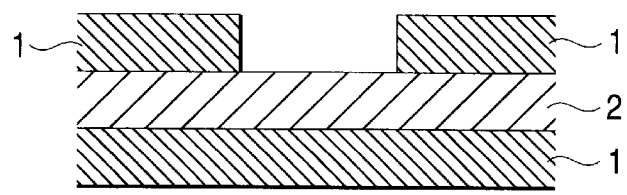

The term "via hole" used in the invention has the same meaning as used usually by those skilled in the art. That is, the term "via hole" means a conducting passage for electrically connecting a plurality of electric conductor layers 1 insulated by at least one electrically insulating layer 2 in the flexible wiring board. The via hole may be provided as a structure in which a non-through hole is filled with an electrically conductive metal as shown in FIGS. 2D and 4E' or may be provided as a structure in which a wall surface of a through hole is plated as shown in FIGS. 3E and 4F'. Any other structure such as a structure (not shown) in which a wall surface of a non-through hole is plated, or a structure formed by a conducting method other than plating such as application of an electrically conductive paste also belongs to the category of the via hole if the structure can serve as the conducting passage.

The material of the electric conductor layer 1 is not particularly limited if the material can be generally used for an electric conductor layer of a flexible wiring board. For example, metal foil of a metal such as copper, gold, stainless steel or nickel or of an alloy of these metals may be used as the material. Especially, copper foil or copper alloy foil is preferred in consideration of elasticity, processability, electrical characteristic, cost, etc.

The material of the electrically insulating layer 2 is not particularly limited if the material can be generally used for an electrically insulating layer of a flexible wiring board. For example, polyethylene terephthalate, polyethylene naphthalate, or polyimide may be used as the material. Especially, polyimide is preferred in consideration of heat resistance, etc.

A method of forming a via hole after forming a non-through hole in a flexible wiring board (FIG. 2A) having two electric conductor layers 1 insulated from each other by an electrically insulating layer 2 will be described as a first embodiment of the invention with reference to FIGS. 2A to 2D. First, the flexible wiring board shown in FIG. 2A is irradiated with an ultraviolet laser beam with energy density (i.e., preferably in a range of from 5 to 20 J/cm², especially preferably in a range of from 6 to 10 J/cm²) suitable for processing one of the electric conductor layers 1. Thus, a structure having a hole formed in the electric conductor layer 1 as the first layer is obtained as shown in FIG. 2B. Then, the structure shown in FIG. 2B is irradiated with an ultraviolet laser beam with energy density (i.e., preferably in a range of from 0.05 to 5 J/cm², especially preferably in a range of from 1.5 to 3 J/cm²) suitable for processing the electrically insulating layer 2. Thus, a structure having a hole formed in the electrically insulating layer 2 as the second layer is obtained as shown in FIG. 2C.

Figure 2C:
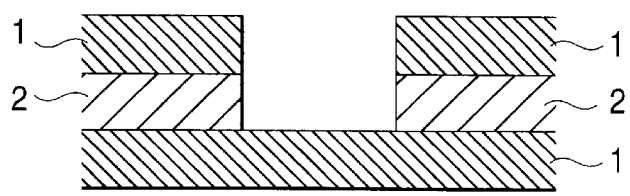
Figure 2D:
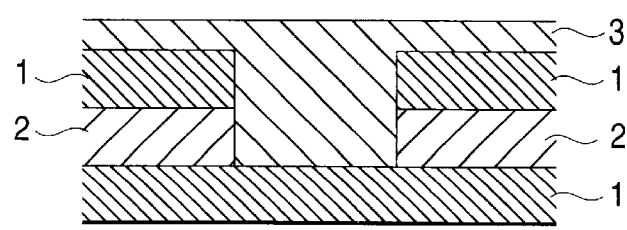

The flexible wiring board shown in FIG. 2C (i.e., the structure having a non-through hole blocked by the electric conductor layer 1 as the third layer) is subjected to a plating process or the like so that the non-through hole is entirely filled. Thus, a flexible wiring board having a via hole filled with an electric conductor metal can be obtained as shown in FIG. 2D.

Although this embodiment has shown the case where the non-through hole is filled with an electric conductor metal by a plating process by way of example, the kind and method of plating are not particularly limited. Any method known by those skilled in the art may be used as the method of plating. As the kind of plating, for example, gold plating, copper plating, nickel plating, or solder plating can be selected. Either electroplating or electroless plating can be used as the method of plating.

When desired circuit patterns are formed in the two electric conductor layers 1 insulated from each other by the electrically insulating layer 2 by a known method such as etching after the via hole is formed as shown in FIG. 2D, a flexible wiring board according to the invention can be obtained. Alternatively, such circuit patterns may be formed before the hole is formed or before the plating process is carried out.

A method of forming a via hole after forming a through hole in a flexible wiring board (FIG. 3A) having two electric conductor layers 1 insulated from each other by an electrically insulating layer 2 will be described as a second embodiment of the invention with reference to FIGS. 3A to 3E. First, a structure having a hole formed in the electric conductor layer 1 as the first layer and in the electrically insulating layer 2 as the second layer as shown in FIG. 3C is obtained from a structure shown in FIG. 3A in the same manner as in the first embodiment. Then, the structure shown in FIG. 3C is irradiated with an ultraviolet laser beam with energy density suitable for processing the electric conductor layer 1 to thereby form a processed hole in the electric conductor layer 1 as the third layer. Thus, a through hole is obtained as shown in FIG. 3D. Then, a wall surface of the through hole is subjected to a plating process in the same manner as in the first embodiment. Thus, a via hole can be obtained as shown in FIG. 3E. Further, desired circuits are formed in the electric conductor layers 1 in the same manner as in the first embodiment. Thus, a flexible wiring board according to the invention can be obtained.

The flexible wiring board according to the invention need not have a three-layer structure as shown in FIGS. 2A to 2D and FIGS. 3A to 3E. That is, the flexible wiring board may have a five-layer structure in which electric conductor layers 1 and electrically insulating layers 2 are laminated alternately as shown in FIGS. 4A to 4F' or the flexible wiring board may have a structure with a larger number of layers (not shown). When the flexible wiring board has a five-layer structure as shown in FIGS. 4A to 4F', a via hole having a structure shown in FIG. 4E' may be formed (by plating at the stage of FIG. 4E) or a via hole having a structure shown in FIG. 4F' may be formed (by plating a wall surface of a through hole shown in FIG. 4F) if the electric conductor layers and the electrically insulating layers are processed by ultraviolet layer beams with energy density in these ranges respectively and plated.

EXAMPLES

Examples of the invention will be described below with reference to the drawings (FIGS. 2A to 2D, FIGS. 3A to 3E and FIGS. 4A to 4F') used in the description of embodiments of the invention but the invention is not limited to the examples. The ultraviolet laser beam used in the invention is the third harmonic of an Nd:YAG laser which is a laser beam with a wavelength of 355 nm. The energy density of irradiation is set by adjustment of "power" and "beam size" of the laser. The "beam size" is adjusted by change of the focus of laser machining apparatus. The energy distribution of the laser beam is adjusted by a micro lens array.

Example 1

In this example, a flexible wiring board shown in FIG. 2A was used. In the flexible wiring board, each of electric conductor layers 1 as first and third layers was made of 9 $\mu$m-thick copper foil, and an electrically insulating layer 2 as a second layer between the two electric conductor layers 1 was made of 25 $\mu$m-thick polyimide.

First, the power, frequency and beam size of the ultraviolet laser beam were set at 0.25 W, 4 kHz and 30 $\mu$mΦ respectively, that is, the energy density of the ultraviolet laser beam was set at 8.8 J/cm² in order to process the electric conductor layer 1 as the first layer. Under this condition, the electric conductor layer 1 was processed by irradiation with the ultraviolet laser beam for 85 msec. Thus, a hole as shown in FIG. 2B was formed in the electric conductor layer 1. Then, the power, frequency and beam size of the ultraviolet laser beam were set at 0.5 W, 7.142 kHz and 55 $\mu$mΦ respectively, that is, the energy density of the ultraviolet laser beam was set at 2.9 J/cm² in order to process the electrically insulating layer 2 as the second layer. Under this condition, the electrically insulating layer 2 was processed by irradiation with the ultraviolet laser beam for 85 msec. Thus, a hole as shown in FIG. 2C was formed in the electrically insulating layer 2.

Electrolytic copper plating was applied to the non-through hole in the structure shown in FIG. 2C so that the deposit on the electric conductor layer 1 became 10 $\mu$m thick. Thus, a flexible wiring board having electrical connection as shown in FIG. 2D was obtained. In the flexible wiring board, there was neither protrusion in the periphery of the processed hole nor defect of uneven precipitation in the plating process.

Example 2

The flexible wiring board used in this example is the same as that used in Example 1. This example will be described with reference to FIGS. 3A to 3E.

Figure 3A:
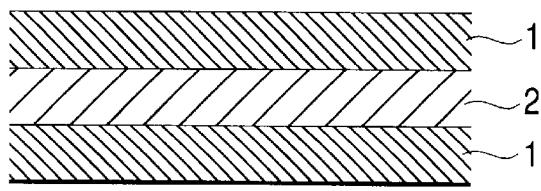
FIGS. 3A to 3E are explanatory views showing another example of the method for forming a via hole according to the invention.
Figure 3B:
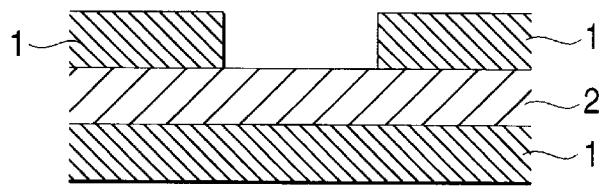
Figure 3C:
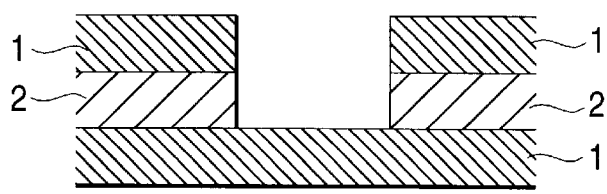
Figure 3D:
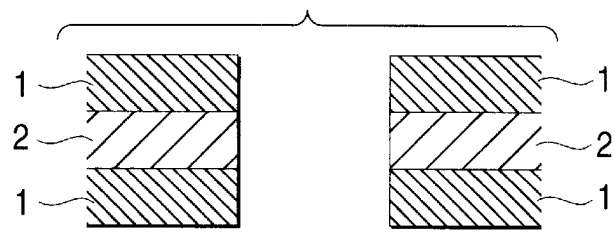
Figure 3E:
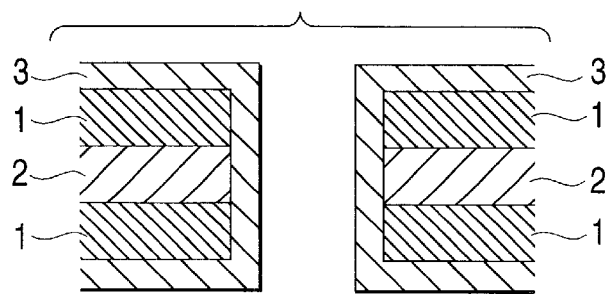

Processing from FIG. 3A to FIG. 3C was carried out in the same manner as in Example 1. In this example, the electric conductor layer 1 as the third layer was further irradiated with an ultraviolet laser beam to thereby form a through hole as shown in FIG. 3D. The condition for processing the third layer was the same as the condition for processing the electric conductor layer 1 as the first layer.

After the through hole was processed, electrolytic copper plating was applied so that the deposit on the electric conductor layers 1 became 10 µm thick. Thus, a flexible wiring board having electrical connection as shown in FIG. 3E was obtained. Also in the flexible wiring board, there was neither protrusion in the periphery of the processed hole nor defect of uneven precipitation in the plating process.

Example 3

This example will be described with reference to FIGS. 4A to 4F'. In this example, a flexible wiring board shown in FIG. 4A was used. In the flexible wiring board, each of electric conductor layers 1 as first, third and fifth layers was made of 9 µm-thick copper foil, and each of electrically insulating layers 2 as second and fourth layers was made of 25 µm-thick polyimide.

Even in the case where the number of layers to be laminated was not three but five, a via hole could be processed according to the invention without any problem. First, processing from the flexible wiring board shown in FIG. 4A to a structure shown in FIG. 4E was carried out by applying the ultraviolet laser beam with energy density in the ranges onto the four layers of two electric conductor layers 1 and two electrically insulating layers 2 alternately by two layers each time. Two flexible wiring boards were produced thus. One of the two flexible wiring boards was prepared for forming a via hole shown in FIG. 4E'. The other was prepared for forming a via hole shown in FIG. 4F'. The two flexible wiring boards were processed as follows.

In the former case, the flexible wiring board in a state shown in FIG. 4E was subjected to electrolytic copper plating so that the deposit on the electric conductor layers 1 became 10 µm thick. Thus, a flexible wiring board having a via hole as shown in FIG. 4E' was obtained. Also in the flexible wiring board, there was neither protrusion in the periphery of the processed hole nor defect of uneven precipitation in the plating process.

On the other hand, in the latter case, the electric conductor layer 1 as the fifth layer in the flexible wiring board in a state shown in FIG. 4E was further irradiated with the ultraviolet laser beam. Thus, a through hole was formed as shown in FIG. 4F. The condition for processing the fifth layer was the same as the condition for processing the electric conductor layers 1 as the first layer and the third layer. Then, the flexible wiring board was subjected to electrolytic copper plating so that the deposit on the electric conductor layers 1 became 10 µm thick. Thus, a flexible wiring board having a via hole as shown in FIG. 4F' was obtained. Also in the flexible wiring board, there was neither protrusion in the periphery of the processed hole nor defect of uneven precipitation in the plating process.

Comparative Example 1

The same processing as processing for the processed hole in Example 1 was carried out while the energy density of the ultraviolet laser beam applied was always set at 8.8 J/cm$^2$ (also for processing the electrically insulating layers 2).

In this case, damage occurred at the stage shown in FIG. 2C so that undulations were observed in the electric conductor layer 1 as the third layer. If such a processed hole was formed, a judgment was made that there was a high probability that connection failure would occur due to generation of cracks in the plating process.

Comparative Example 2

The same processing as processing for the processed hole in Example 1 was carried out while the energy density of the ultraviolet laser beam applied was always set at 2.9 J/cm$^2$ (also for processing the electric conductor layer 1). In this case, the time required for processing the electric conductor layers 1 became long (a processing time of 85 msec was required in Example 1 whereas a processing time of 2 sec was required in Comparative Example). In addition, protrusions were observed in the periphery of the processed hole in the electric conductor layer 1 as the first layer.

Comparative Example 3

The same processing as processing for the processed hole in Example 2 was carried out while the energy density of the ultraviolet laser beam applied was always set at 8.8 J/cm$^2$ (also for processing the electrically insulating layers 2).

In this case, micro cracks occurred in the electrically insulating layer 2 at the stage shown in FIG. 3D because of processing with 8.8 J/cm$^2$. As a result, barrel cracks (a broken state caused by insufficient plating on a side surface of the processed hole) occurred in the plating process. If such a flexible wiring board was used, there was fear that failure might occur in a post-process.

Comparative Example 4

The same processing as processing for the processed hole in Example 2 was carried out while the energy density of the ultraviolet laser beam applied was always set at 2.9 J/cm$^2$ (also for processing the electric conductor layer 1).

In this case, the time required for processing the electric conductor layers 1 became long like Comparative Example 2. In addition, micro cracks occurred in the electrically insulating layer 2 because of heat accumulated in the inside of the hole when the electric conductor layer 1 as the third layer was processed. If such a through hole was formed, there arose a problem that barrel cracks occurred to reduce the reliability of the via hole after plating.

When a flexible wiring board having a five-layer structure as shown in FIGS. 4A to 4F' was irradiated with the ultraviolet laser beam under the conditions as described in Comparative Examples 1 to 4, it was confirmed that failure described in Comparative Examples 1 to 4 occurred in accordance with the shape of the via hole and the energy density of the ultraviolet laser beam.

According to the invention, excessive heat energy applied for forming a via hole can be reduced. As a result, the problem which has occurred in the related-art via hole can be reduced, so that quality can be improved. In this manner, improvement in quality of the via hole, and delicate and accurate processability due to use of an ultraviolet laser beam can be combined to achieve formation of fine patterns densely in the flexible wiring board. In addition, improvement in reliability of electrical connection due to the via hole can be expected. The flexible wiring board is expected to contribute to greater reduction in weight and thickness of electronic apparatus and greater increase in density in the electronic apparatus.

What is claimed is:

1. A method of forming a via hole in a flexible wiring board having at least two electric conductor layers and at least one electrically insulating layer for insulating said two electric conductor layers from each other, said method comprising:

irradiating one of said electric conductor layers with a first ultraviolet laser beam; and irradiating said electrically insulating layer with a second ultraviolet laser beam;

wherein energy density of said first ultraviolet laser beam is higher than energy density of said second ultraviolet laser beam.

2. A method of forming a via hole in a flexible wiring board according to claim 1, wherein energy density of said first ultraviolet laser beam is selected to be higher by a value ranged from 0.1 to 20 J/cm$^2$ than energy density of said second ultraviolet laser beam.

3. A method of forming a via hole in a flexible wiring board according to claim 1, wherein energy density of said first ultraviolet laser beam is selected to be in a range of from 5 to 20 J/cm$^2$, whereas energy density of said second ultraviolet laser beam is selected to be in a range of from 0.05 to 5 J/cm$^2$.

4. A method of forming a via hole in a flexible wiring board according to claim 1, said method comprising the steps of:

irradiating a via hole-forming portion of said one of said electric conductor layers with said first ultraviolet laser beam to thereby form an opening in said one electric conductor layer; and subsequently irradiating said electrically insulating layer with said second ultraviolet laser beam to thereby form an opening in said electrically insulating layer after forming the opening in said one electric conductor.

5. A method of forming a via hole in a flexible wiring board by repeating the steps defined in claim 4.

6. A method of forming a via hole in a flexible wiring board according to claim 1, said method comprising the steps of:

irradiating a via hole-forming portion of a first layer of said electric conductor layers with said first ultraviolet laser beam to thereby form an opening in said first electric conductor layer; and irradiating said electrically insulating layer with said second ultraviolet laser beam to thereby form an opening in said electrically insulating layer; and irradiating a second layer of said electric conductor layers which is located on opposite side to said first electric conductor layer with respect to said electrically insulating layer with said first ultraviolet laser beam to thereby form an opening in said second electric conductor layer, whereby said openings are formed as the via hole in said flexible wiring board.

7. A method of producing a flexible wiring board, including a method defined in any one of claims 1 through 6.

* * * * *